United States Patent [19]

Bullara

[11] 4,127,110
[45] Nov. 28, 1978

[54] IMPLANTABLE PRESSURE TRANSDUCER

[75] Inventor: Leo A. Bullara, Glendora, Calif.

[73] Assignee: Huntington Institute of Applied Medical Research, Pasadena, Calif.

[21] Appl. No.: 689,169

[22] Filed: May 24, 1976

[51] Int. Cl.² .............................................. A61B 5/00
[52] U.S. Cl. .................................... 128/2 P; 73/718; 73/729; 128/2.05 E
[58] Field of Search ............... 128/2.1 A, 2 P, 2.05 P, 128/2.05 E; 73/398 R, 398 C, 399, 410; 325/67, 118; 324/40

[56] References Cited

U.S. PATENT DOCUMENTS

| 3,034,356 | 5/1962 | Bieganski et al. | 128/2 P |
| 3,135,914 | 6/1964 | Callan et al. | 324/40 |
| 3,943,915 | 3/1976 | Severson | 128/2 P |
| 3,958,558 | 5/1976 | Dunphy et al. | 128/2 P |
| 4,022,190 | 5/1977 | Meyer | 128/2 A |
| 4,026,276 | 5/1977 | Chubbuck | 128/2 P |
| 4,027,661 | 6/1977 | Lyon et al. | 128/2 A |

OTHER PUBLICATIONS

Atkinson, J. R., et al., *Journ. of Neurosurgery*, vol. 27, No. 5, 1967, pp. 428–432.
*Medical Engineering*, Ch. 15, C. R. Ray, Yearbook Publishing, Chicago, 1974, p. 156.

*Primary Examiner*—Kyle L. Howell
*Attorney, Agent, or Firm*—Christie, Parker & Hale

[57] ABSTRACT

A wireless, surgically implantable pressure transducer for measuring pressure of fluid or tissue in a body chamber such as a brain ventricle of a patient suffering hydrocephalus or a head injury. The transducer includes an inductor and a capacitor connected in parallel to form a resonant L-C circuit. One of these reactive components is variable, and a bellows (or similar pressure-sensitive force-summing device) is mechanically connected to the variable component to vary the value of capacitance or inductance and hence the resonant frequency of the L-C circuit in response to pressure changes of the fluid in which the bellows is immersed. The transducer is electromagnetically coupled to an external source of variable-frequency energy such as a grid-dip oscillator, enabling external detection of the transducer resonant frequency which is a measure of the fluid pressure being sensed. An antenna coil is inductively coupled to the transducer inductor, and is positioned in the transducer to be just beneath the skin when the housing is implanted to provide efficient coupling of the external oscillator and internal resonant circuit. A second bellows or analogous device may be coupled to a reference-pressure side of the transducer to provide improved compensation of variations in ambient temperature and atmospheric pressure.

13 Claims, 12 Drawing Figures

IMPLANTABLE PRESSURE TRANSDUCER

BACKGROUND OF THE INVENTION

Hydrocephalus is a brain condition in which cerebrospinal fluid accumulates at abnormally high pressure in ventricles or chambers within the brain. The ventricles expand in response to the pressure exerted by the fluid, and surrounding brain tissue is compressed between the ventricles and the skull. Hydrocephalus usually occurs in babies or young children, and, if unchecked, results in brain damage, enlargement and deformation of the head, and eventual death.

Modern medical methods are effective in arresting many cases of hydrocephalus, but it is often desirable to monitor pressure of the cerebrospinal fluid over an extended period to detect relapse and to determine longrange effectiveness of treatment. In the past, this measurement has been made by surgically implanting a miniature but generally conventional transducer such as a straingage-bridge pressure pickup. This technique requires that wiring be conducted from the implanted transducer to external instrumentation which provides excitation voltage to the bridge and detects bridge-unbalance voltage signals indicative of pressure. Alternatively, non-electrical manometric measurement methods may be used, but these techniques require installation of a conduit extending from the interior of the brain ventricle through the skull and scalp to external measurement equipment.

The primary disadvantage of these known techniques is that they involve conducting an electrical cable or fluid tube through the skull and scalp to enable direct electrical or mechanical connection between the interior of the brain ventricle and external equipment. This connection is disturbing and uncomfortable for the patient, and the danger of infection of tissue surrounding the cable or tube (and the risk of infection spread resulting in meningitis, ventriculitis, brain abscess or septicemia) requires constant supervision and usually full-time hospitalization of the patient. There is accordingly a need for a measuring device which does not require direct electrical or mechanical connection from the brain to external equipment, and which permits the patient to be ambulatory after the device is installed.

Connection-free implantable transducers have been previously proposed, and they typically function by external detection of the resonant frequency of a resonant circuit in the implanted device. For example, the prior art includes a biological pressure transducer for sensing pressure in the gastrointestinal tract and having a resonant circuit with a pressure-controlled inductor. Wireless systems are also used for sensing EEG or ECG voltages, the implantable part of the system using an electrically variable capacitor in a resonant circuit. A wireless resonant-circuit transducer has also been used for measuring intraocular pressure, the transducer using a pair of variably spaced Archimedean-spiral coils mounted on pressure-sensitive diaphragms.

The transducer of this invention operates in wireless fashion similar to the instruments described above, but provides improved performance and lower drift in implantation applications involving placement in body cavities such as brain ventricles, bladder, or heart chambers were only a very small transducer can be tolerated. The transducer is disclosed below in a specific form suitable for intracranial implantation to monitor pressure of cerebrospinal fluid in a brain ventricle. This form is also suitable for mounting on hydrocephalus shunt apparatus as often used in treating and controlling this disease.

The transducer is also suitable for implantation elsewhere in the body or in other systems, and is believed useful in any application where a very small wireless device is needed to measure fluid or tissue pressure. For example, the transducer is believed useful for either short- or long-term monitoring of abnormal intracranial pressure in headinjury patients, or for post-surgical monitoring of braintumor victims to detect possible recurrence of the tumor. When such monitoring is no longer needed, the implanted transducer is removed by a simple re-opening and closure of the overlying scalp tissue.

CROSS REFERENCE TO RELATED APPLICATION

The invention herein disclosed is an improvement of subject matter disclosed in copending U.S. patent application Ser. No. 506,217 filed Sept. 16, 1974 by applicant and others, now U.S. Pat. No. 3,958,558.

SUMMARY OF THE INVENTION

Briefly stated, this invention relates to improvements in transducers which are preferably of an implantable type having a resonant L-C circuit with capacitor and inductor elements, one of which is variable and driven by a mechanical force sensor such as a bellows or similar pressure-sensing means. The circuit has a variable resonant frequency related to the magnitude of force imposed on the sensor, and this resonant frequency can be determined in wireless fashion by an external interrogating device such as a variable-frequency grid-dip oscillator. In the forms disclosed below, the transducer is intended for measuring fluid in a body cavity such as cerebrospinal fluid in a brain ventricle, but the transducer is not limited to this particular application.

In one form, the transducer inductor element includes a coil wound on a hollow tubular mandrel, and a ferrite core positioned within the mandrel and driven by the force sensor. A coupling coil is wound adjacent the inductor coil, and is electrically connected to a remotely positioned antenna coil disposed in a portion of a housing for the transducer which is close to the patient's skin when the transducer is used as an implantable device. Preferably, the coupling and antenna coils have the same number of turns, but the antenna coil is larger in diameter than the coupling coil for efficient inductive coupling with an external antenna associated with the interrogating equipment.

The transducer may also include a pressure-sensing variable-volume means such as a second bellows which is in fluid connection with a sealed volume within the transducer to define a reference pressure for the transducer. The purpose of the second bellows is to reduce or eliminate transducer errors arising from unwanted response to variations in barometric pressure or ambient temperature. In one form the two bellows are substantially identical, and are rigidly connected together by a shaft or similar means. In another form, the two bellows are not mechanically connected, but are of unequal diameter and stiffness, the second bellows having the larger diameter and lower stiffness.

These improvements enable the overall transducer system to have improved sensitivity and better coupling with external equipment, and a significant reduction in sensitivity to environmental variations is achieved.

DESCRIPTION OF THE PREFERRED EMBODIMENTS

Figure 1:
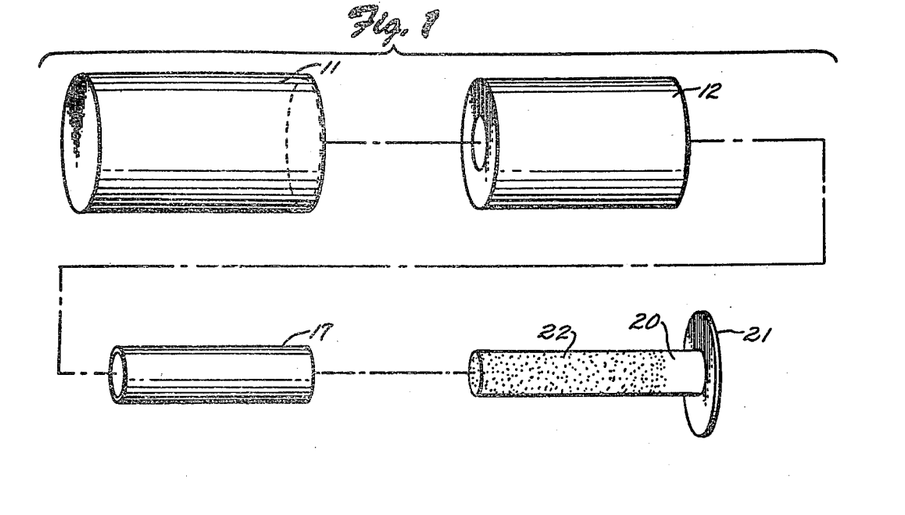
FIG. 1 is an exploded view of a portion of a pressure transducer according to the invention.
Figure 2:
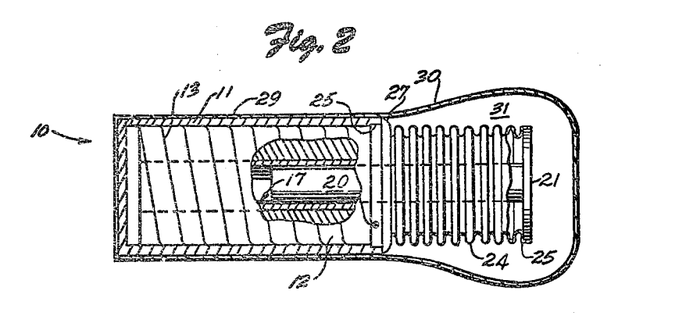
FIG. 2 is a side elevation, partly in section, of the assembled transducer.

Referring to FIGS. 1-2, a pressure transducer 10 according to the invention includes a housing 11 which is preferably a hollow cylindrical cup of cast epoxy resin as sold under the trademark "Hysol". In a typical form, the housing is 0.550-inch long, and has outside and inside diameters of 0.275 and 0.260-inch respectively.

A hollow cylindrical ferromagnetic core 12 is sized to make a loose fit within housing 11, and the core is typically 0.500-inch long, with outside and inside diameters of 0.250 and 0.125-inch respectively. The core is preferably made from a sintered ferrite material such as sold by Indiana General Division of Electronic Memories Magnetics Corporation as "Q-2 Ferramic" material.

Figure 4:
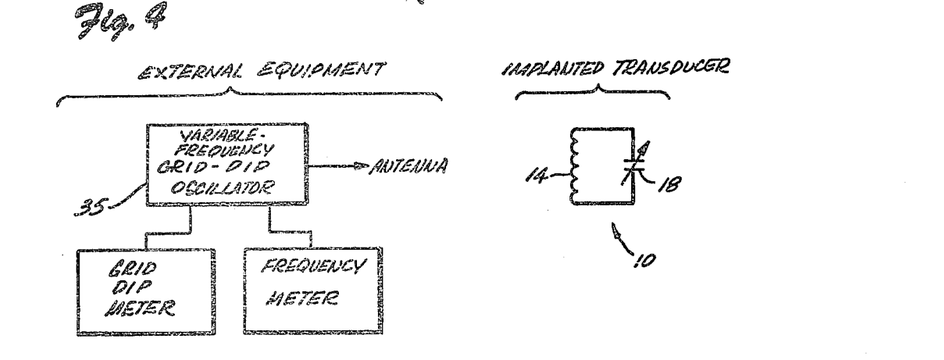
FIG. 4 is a block diagram of external electronic equipment used with the transducer.

A coil 13 (FIG. 2) is formed by helically wrapping about 10 turns of a conductor such as 0.020-inch-diameter gold wire around the outside surface of core 12. Core 12 and coil 13 form an inductor 14 for the transducer as shown in the electrical schematic in FIG. 4.

A hollow cylindrical sleeve 17 (FIGS. 1-2) of a nonferrous material such as brass forms a fixed electrode of a coaxial variable capacitor 18 (FIG. 4) in transducer 10. The sleeve is sized to make a snug slip fit within core 12, and is typically 0.400-inch long with outside and inside diameters of 0.124 and 0.100-inch respectively.

A rod or piston 20, having a thin, integrally formed and radially extending flange 21 at one end, is also made from a non-ferrous material such as brass. A portion of the outside of the rod is covered with a thin dielectric coating 22 of a material such as tantalum pentoxide. The piston fits into sleeve 17 in piston-cylinder fashion, and forms a movable element or electrode of coaxial variable capacitor 18. The piston has an overall length of about 0.500-inch, and the piston and flange have diameters of about 0.095 and 0.020-inch respectively.

A generally cylindrical bellows 24 (FIG. 2) provides a force-summing surface for transducer 10, the bellows varying in length according to the pressure of fluid in which the transducer is immersed. A typical and suitable bellows is sold by Servometer Corporation as a Type SK4681. The bellows is made of an electrically conductive material which is preferably gold-plated nickel. The ends of the bellows are open, and each end defines an axially extending shell or flange 25.

To assemble the transducer, capacitor sleeve 17 is cemented within core 12, the left ends (as viewed in FIG. 2) of these components being flush. The left end of coil 13 is drawn around the end of core 12 and soldered into electrical contact with the sleeve. Flange 25 at the left end of bellows 24 is then slipped over the right end of core 12 and cemented in place. The right end of coil 13 is soldered or otherwise bonded into electrical contact with the bellows flange as shown in FIG. 2.

Capacitor piston 20 is then fitted through the bellows into sleeve 17, and flange 21 of the piston is secured within flange 25 at the right end of the bellows, the attachment being made with an electrically conductive cement such as a conductive silver-epoxy or gold-epoxy adhesive. The capacitor piston is thus electrically connected to the right end of coil 13 through bellows 24. Sealing of the transducer is completed by placing an annular body 27 of epoxy resin or a similar sealant between the right end of housing 11 and the bellows.

The transducer interior is hermetically sealed from the outside environment so fluid cannot seep into the bellows or variable coaxial capacitor. Preferably, the transducer is evacuated prior to final sealing, and is back-filled with dry nitrogen. Back-filling is normally done at one atmosphere of pressure to provide a transducer which functions as a "sealed gage pressure" measuring device, but other pressures may be used if a reference pressure other than one atmosphere is preferred.

Preferably, housing 11 is sheathed in a covering 29 of a biologically compatible material such as plastic sold under the trademark "Silastic". In a preferred embodiment, covering 29 is extended to form a loose balloon-like enclosure 30 around bellows 24, and enclosure 30 is filled with distilled water 31, or preferably with a fluid which approximates the composition of the fluid being monitored (such as Elliot's 'B' solution when cerebrospinal fluid is being monitored) to provide a correct ionic balance on both sides of the enclosure. Pressure of the fluid being monitored is transmitted through enclosure 30 and water 31 to actuate bellows 24, but the enclosure and water form a chemical and mechanical buffer preventing tissue encroachment which could interfere with free compression and extension of the bellows.

Figure 3:
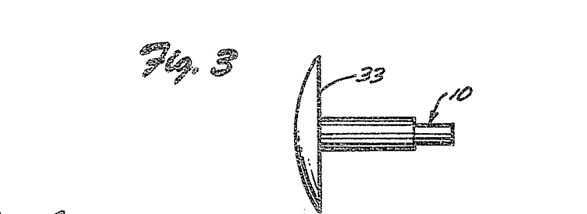
FIG. 3 is a side elevation of the transducer mounted on a plug for intracranial installation.

When used as an intracranial implant in a brain ventricle or in brain tissue, transducer 10 is preferably mounted on a flanged plug 33 of a material such as "Silastic" plastic. Surgical installation of this equipment involves generally the same procedures used in installing hydrocephalus shunts or pressure absorbers, these procedures being briefly discussed in U.S. Pat. No. 3,583,387—Garner and Bullara titled "Pressure Absorbing Appliance for Treating Hydrocephalus".

The values of inductance and capacitance of the parallelconnected inductor and capacitor of transducer 10 can be computed and pre-determined using known engineering formulae. Circuits having nominal resonant frequencies in the range of about 30 to perhaps 100 megaHertz are believed best suited for biological applications. Higher frequencies (e.g., 200 mHz) have some advantages, but low "Q's" typically experienced in tissue at these frequencies tend to obscure the accurate external detection of resonance of the transducer L-C circuit.

Pressure range of the transducer is determined primarily by the mechanical performance of bellows 24, and these displacement-versus-pressure characteristics can also be calculated by known engineering formulae. Typical units which have been tested had an operating pressure range of 0 to 1000 millimeters of water (gage), and the transducer L-C circuit has been designed to have a zero-pressure resonant frequency of about 82 mHz. As the fluid pressure is increased, bellows 24 contracts to drive capacitor piston 20 into sleeve 17, thereby increasing the capacity of the coaxial capacitor and decreasing the resonant frequency of the circuit. A change in resonant frequency of about 20 mHz is typically obtained in driving the transducer from zero to full-scale pressure.

In use, the installed transducer is irradiated with electromagnetic energy transmitted through the body and generated by an external variable-frequency oscillator. Some of this radio-frequency energy is absorbed (and also reflected or retransmitted) by the resonant circuit, depending on how close the incident frequency is to the resonance frequency of the circuit. The frequency of the external oscillator is varied or swept until resonance of the transducer L-C circuit is externally detected. This resonant frequency is in turn indicative of the internal fluid pressure being sensed by the transducer.

A simple and accurate way to detect internal transducer resonance with an external circuit involves use of a griddip oscillator 35 (FIG. 4) which shows a sharp drop or "valley" in grid current when the resonant point of the "receiving" circuit is swept through by the "transmitting" oscillator. The oscillator is preferably used in conjunction with a conventional electronic frequency counter which provides a direct visual readout of frequency at the resonant point.

External phase-sensitive equipment can also be used to detect the characteristic and marked phase shift which occurs when the resonant circuit receives energy at its resonant frequency. Other external detection systems are discussed in the literature, such as IEEE Transactions on Bio-Medical Engineering, Volume BME 14, No. 2, pages 74–83, April 1967, and the references therein cited.

Prior to installation, the transducer is calibrated by immersing it in a fluid (e.g., Elliot's 'B' solution) having characteristics similar to the biological fluid or tissue to be eventually monitored. The pressure of the test fluid is then varied under controlled conditions while the resonant frequency of the transducer is tracked as described above to develop a pressure-versus-frequency calibration curve.

The transducer of this invention can also be made with a variable-reactance element which is a coaxial variable inductor connected across a fixed capacitor, or both the capacitive and inductive components can be variable under control of the pressure-sensitive bellows. A variable-inductor embodiment of the invention is shown as a transducer 40 in FIG. 5.

Figure 5:
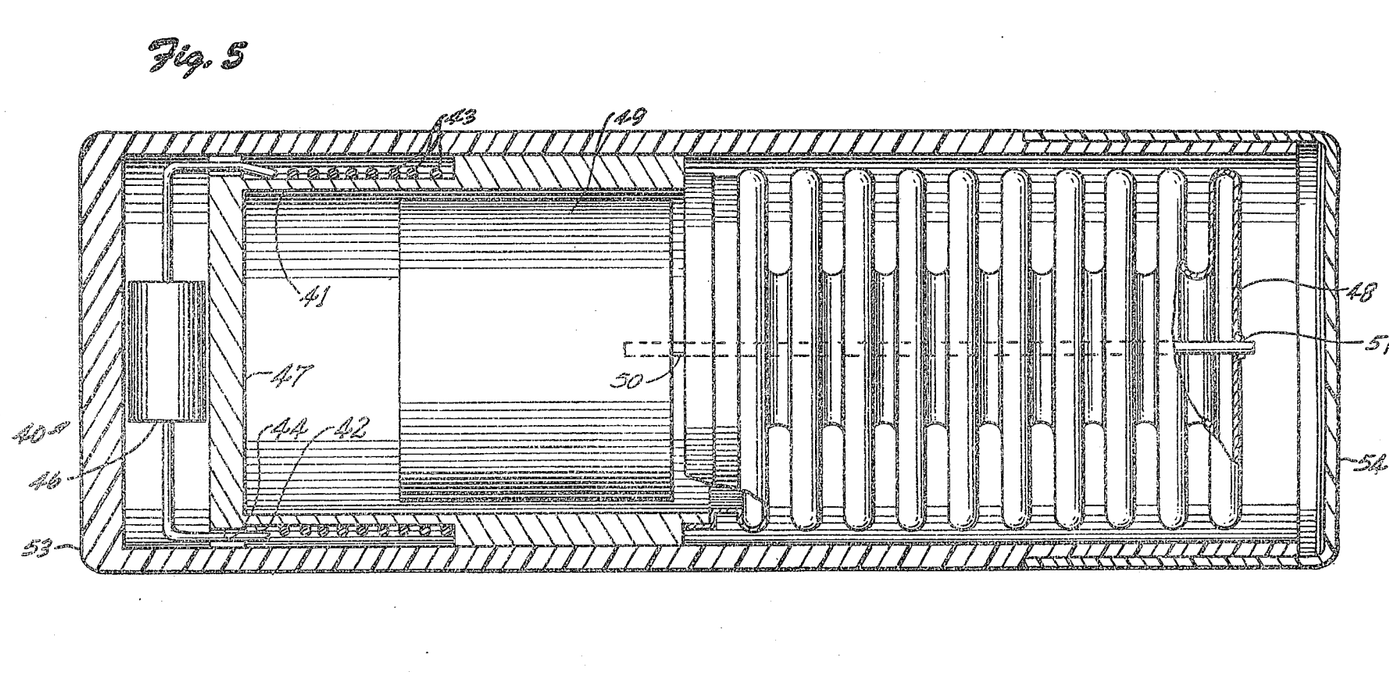
FIG. 5 is a side sectional elevation of a first alternative transducer according to the invention and using a variable inductor.

Transducer 40 includes a cup-shaped hollow cylindrical coil-supporting sleeve 41 which is preferably made of polytetrafluorethylene plastic or a medical-grade acrylic plastic. The sleeve has an annular recess 42 in which is wound an inductive coil 43 of say 12 turns of 0.005-inch-diameter copper or gold insulated wire. The ends of the coil are fed through a pair of longitudinal slots 44 at one end of sleeve 41 for connection to a miniature fixed capacitor 46 mounted on a wall 47 which closes one end of the sleeve. The coil and capacitor are preferably "potted" in a medical-grade paraffin (not shown).

A bellows 48 (generally corresponding to bellows 24 described above) is fitted over and secured to the open end of sleeve 41. A solid cylindrical ferrite core 49 is positioned within sleeve 41 to form an inductor with coil 43. A stiff metal shaft 50 (preferably a length of stainlesssteel tubing of about 0.009-inch outside diameter as used in hypodermic needles) is secured to the core and extends therefrom through a central opening 51 in the closed end of bellows 48. During assembly of the transducer, the "zero" position of the core is adjusted to provide a desired inductance of the coil and core, and shaft 50 is then permanently secured to the bellows to support the core.

A cup-shaped housing 53 made of medical-grade acrylic plastic is slipped over and secured to sleeve 41. An enclosure 54 is fitted over and sealed to the open end of housing 53, and this enclosure is preferably a membrane of "Silastic" plastic material. The space between the outer surface of the bellows and the inner surfaces of the membrane and housing is filled with distilled water or a fluid compatible with the characteristics of the fluid being monitored as described above.

The dimensions of housing 53 are about 0.165-inch diameter by 0.445-inch length, and a very compact assembly is provided which is suitable for implantation. A nominal resonant frequency of about 80 mHz is provided by using a capacitor of 5 picofarads and an inductance of about 0.8 microhenries. Installation and use of transducer 40 corresponds to the procedures discussed above with respect to transducer 10.

Figure 6:
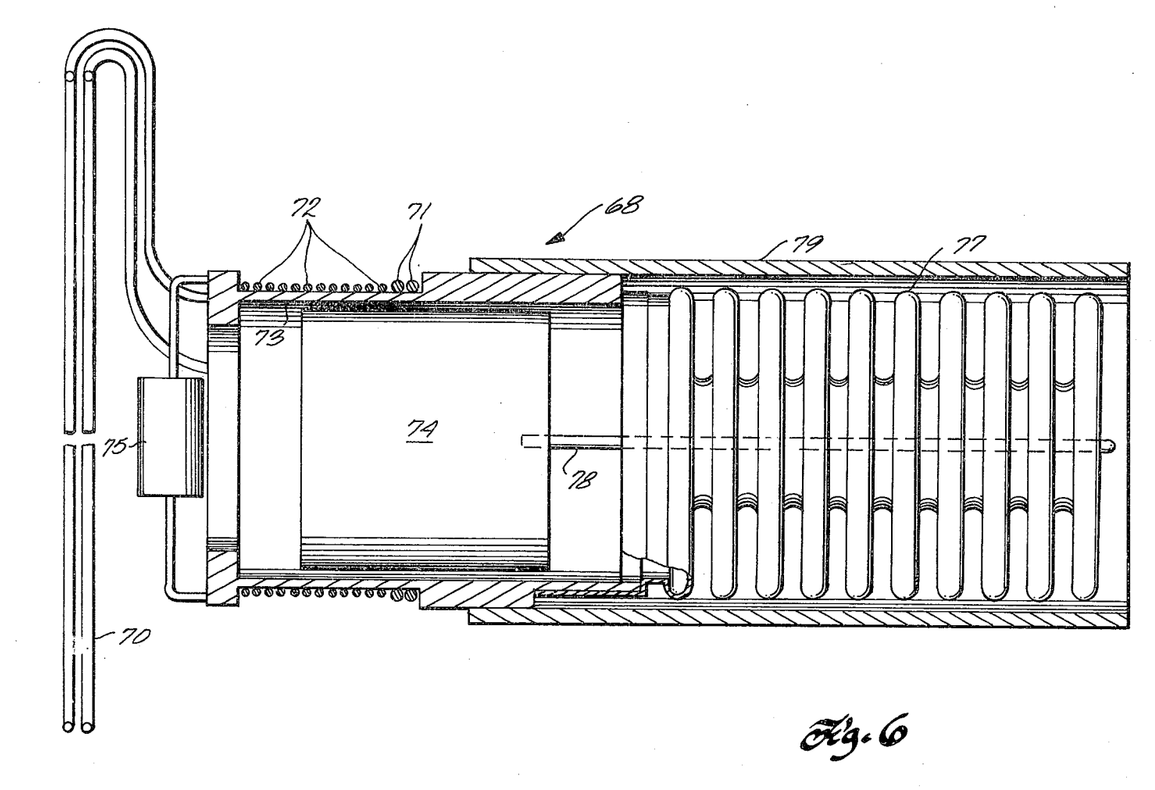
FIG. 6 is a side elevation, partly in section, of a second alternative transducer subassembly using an antenna coil.

A more sensitive embodiment of the invention includes a transducer subassembly 68 in FIG. 6, and is characterized by the use of an antenna coil 70 connected to a coupling coil 71 which is inductively coupled to an inductor coil 72 wound on an open-ended mandrel or hollow sleeve 73. A solid cylindrical ferrite core 74 is movably positioned within sleeve 73 to form a variable inductor with coil 72. A capacitor 75 is connected across inductor coil 72 to provide a variable-resonant-frequency L-C circuit.

A pressure-sensitive bellows 77 is secured and sealed over an open end of sleeve 73, and a shaft 78 is secured to the closed distal end of the bellows and to core 74. Motion of the bellows in response to pressure changes is thus transmitted to the core to vary the inductance and the resonant frequency of the L-C circuit as already described.

An acrylic-plastic shield sleeve 79 may be fitted over and secured to the bellows end of sleeve 73 to extend over the side surfaces of the bellows to prevent tissue interference with the bellows. Holes (not shown) may be formed in the sidewall of the shield sleeve to insure free fluid circulation around the bellows. The distal end of the shield sleeve is open, and the inner wall of the shield sleeve is radially spaced from the bellows sidewall to insure free movement of the bellows responsive to pressure changes.

Figure 7:
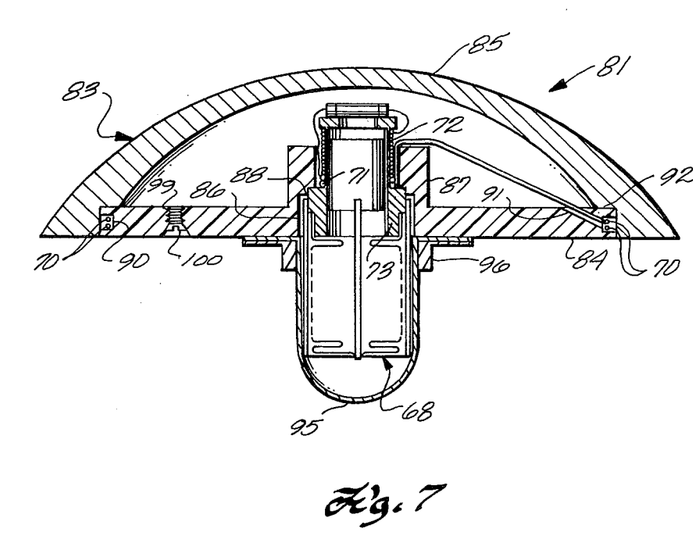
FIG. 7 is a sectional elevation of the second alternative transducer subassembly mounted to measure epidural pressure.

The L-C circuit components with bellows 77 and sleeve 73 (and optionally sleeve 79, depending on the application) form transducer subassembly 68 which can be mounted in several ways depending upon the geometry of the space in which fluid pressure is to be measured. In an epidural configuration 81 as shown in FIG. 7, the transducer subassembly is seated in a hollow dome-shaped housing 83 which includes a base 84 and a cover 85.

Base 84 is a flat circular plate of an implantable material such as acrylic plastic, and an opening 86 is formed in the center of the plate. A tubular extension 87 is integrally formed with the plate around opening 86, and the extension defines an inwardly extending annular flange 88 against which hollow sleeve 73 of the transducer subassembly is seated. An annular groove 90 is formed in the sidewall of base 84, and antenna coil 70 is wound in this groove. The ends of the antenna coil are fed through a shallow clearance groove 91 in the base to extend over the base to the transducer subassembly into connection with coupling coil 71.

Cover 85 is generally circular in planform, and is inwardly concave to receive the transducer subassembly. An annular shoulder 92 is formed in the undersurface of the cover, and base 84 is seated against this shoulder. The cover, base, and transducer subassembly are preferably cemented together, and an epoxy coating is preferably provided along the entire undersurface of the base and dome to resist fluid leakage from the space in which the transducer is immersed. Cover 85 is preferably formed from acrylic plastic.

A thin and flexible cap-shaped diaphragm 95 of "Silastic" plastic or a comparable sheet material surrounds the transducer bellows, and is secured in place by a clamping ring 96 cemented to the housing base. The space between the bellows and diaphragm is filled with Elliot's 'B' solution or a comparable fluid as explained above.

The interior of the transducer assembly is vented through the open inner end of hollow sleeve 73 to be in communication with the sealed interior volume of housing 83. A relatively large reference-pressure volume is thus provided for the transducer. A small threaded hole 99 may be formed through base 84 to vent this volume during assembly, and the opening is subsequently closed with a screw 100 which is sealed with cement with the reference pressure stabilized at say one atmosphere.

In a typical configuration, inductor coil 72 is about 12 turns of 40-gage enameled copper wire wound in a single layer on a mandrel outside diameter of 0.109 inch. Coupling coil 71 is two turns of 32-gage enameled copper wire wound on the same mandrel diameter immediately adjacent the end of the inductor coil closest to the bellows. This arrangement positions the coupling coil around movable ferrite core 74 throughout the full range of movement of the core, whereby the inductance of the coupling coil is substantially unaffected by core movement. The core extends only partially into inductor coil 72 because a significant change in inductance is desired to insure an easily measurable shift in resonant frequency of the L-C circuit in response to bellows movement arising from pressure changes.

Antenna coil 70 is matched to coupling coil 71 with respect to number of turns, and is hence typically two turns of the same 32-gage wire used to form the coupling coil. The antenna coil, has a significantly larger diameter than that of the coupling coil, and the diameter of the base of groove 90 (forming a mandrel for the antenna coil) is typically about 0.778 inch. In a unit which has been tested, the nominal inductance and capacitance values of the L-C circuit were 0.65 microhenries and 2 picofarads, providing a nominal resonant frequency of about 140 mHz.

The transducer assembly and housing is surgically installed as discussed above to be fully implanted without need for wired or tubing connections to external equipment. When used to measure intracranial pressures, a small hole is formed through the skull, and the bellows "shank" of the transducer is fitted into the skull opening. Base 84 and domed cover 85 are seated against the skull, and the overlying scalp is then sutured to close the incision and seal the transducer assembly under the skin. Interrogation of the transducer to detect the resonant frequency is made with a grid-dip oscillator or other sensing devices such as a pulse generator and phase-shift detector.

Figure 10:
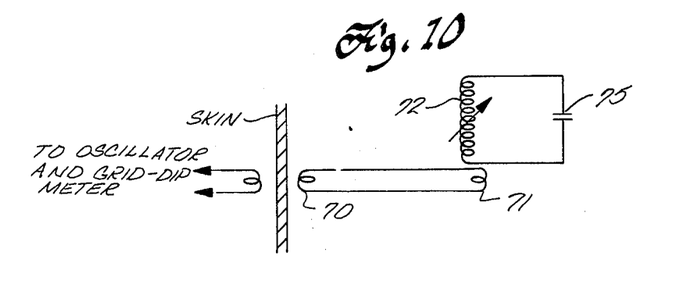
FIG. 10 is a schematic diagram of the measurement system.

The antenna and coupling coils in effect form an inductive link between the transducer subassembly and an external transmitting-antenna coil of a grid-dip oscillator (illustrated schematically in FIG. 10) used as already described to sense the resonant frequency of the L-C circuit which is in turn indicative of the fluid pressure being sensed. The relatively large diameter of antenna coil 70 provides good inductive coupling with the transmitting-antenna coil of the external grid-dip oscillator, and the small diameter of coupling coil 71 insures good coupling with inductor coil 72. The result is a significant increase in overall system sensitivity and "Q" or sharpness of the resonant frequency of the L-C circuit.

Figure 8:
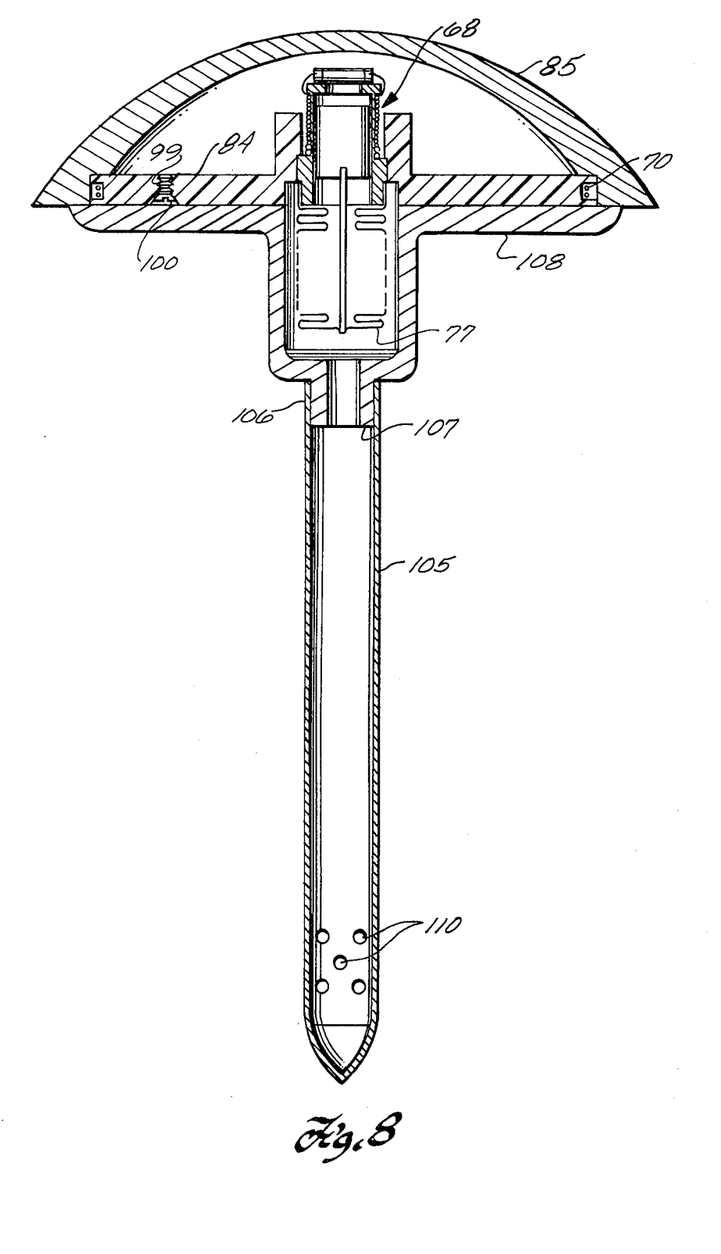
FIG. 8 is a view similar to FIG. 7, but including a ventricular cannula.

The epidural configuration just described is readily modified to measure intraventricular fluid pressure by adding a hollow elongated cannula 105 as shown in FIG. 8. One end 106 of the cannula is fitted over and secured to a tubular extension 107 of a hollow annular adapter plate 108 cemented and sealed to the floor of base 84 and cover 85. Holes 110 in the distal end of the cannula permit cerebrospinal fluid in the ventricle to fill the interior of the cannula, the fluid pressure thus being sensed by bellows 77 of transducer subassembly 68.

An equally important feature of the antenna and coupling coils is that positioning of the transducer subassembly within the body can be varied without affecting performance of the transducer system. For example, it may be desirable to position the transducer subassembly deeply into a brain ventricle at a significant spacing from the scalp. The antenna coil, however, remains positioned immediately below the scalp for good coupling to the grid-dip oscillator, and the wires connecting the antenna and coupling coils are simply lengthened as necessary to accommodate the spacing of the transducer subassembly from base 84 and cover 85.

Figure 9:
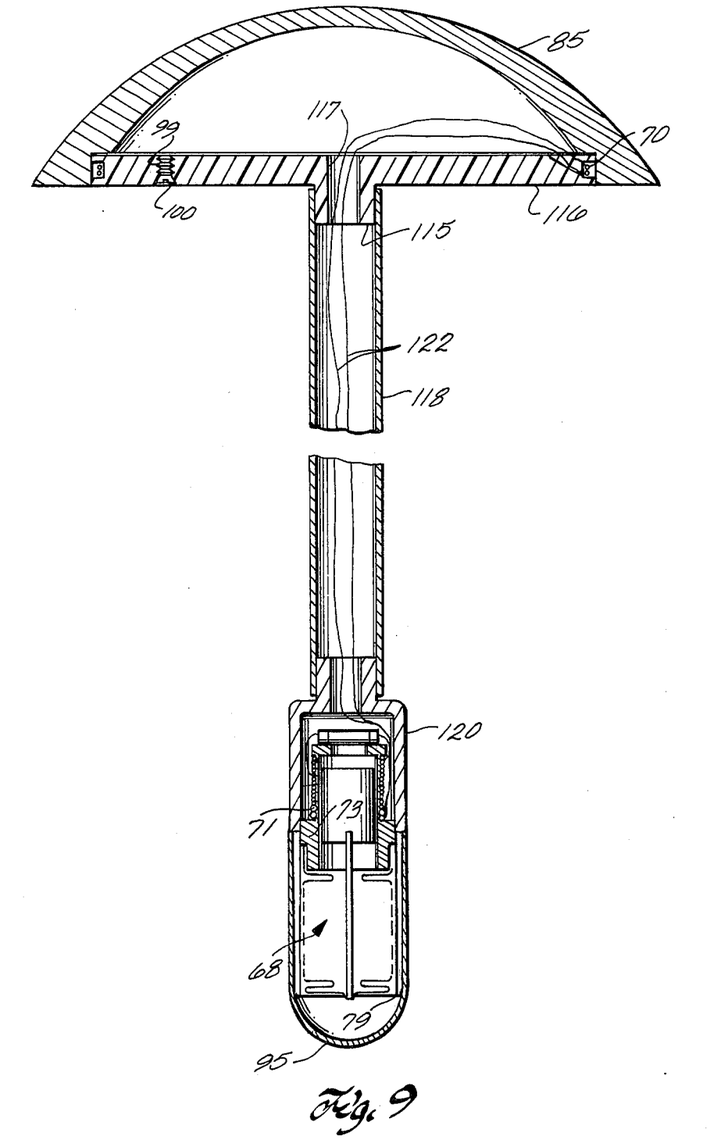
FIG. 9 is a view similar to FIG. 7, but showing the transducer subassembly mounted for positioning in a ventricle.

An example of this arrangement is shown in FIG. 9 which depicts a transducer subassembly 68 arranged to measure pressure directly in a cavity remote from the skin. A tubular boss 115 is formed on a modified housing base 116 having a central opening 117. An extension tube 118 is secured to boss 115 and a generally cylindrical transducer housing shell 120 is secured at the distal end of the extension tube. The outer surface of sleeve 73 of the transducer subassembly is cemented in sealed fashion to the inner surface of housing shell 120. Elongated wires 122 extend through extension tube 118 to connect coupling coil 71 with antenna coil 70 which is wrapped around the periphery of base 116. This arrangement is advantageous in that fluid pressure is measured in the area of interest, and the measurement is unaffected by the position of the patient's body (i.e., the effect of gravity on the column of fluid in the cannula shown in FIG. 8).

Figure 11:
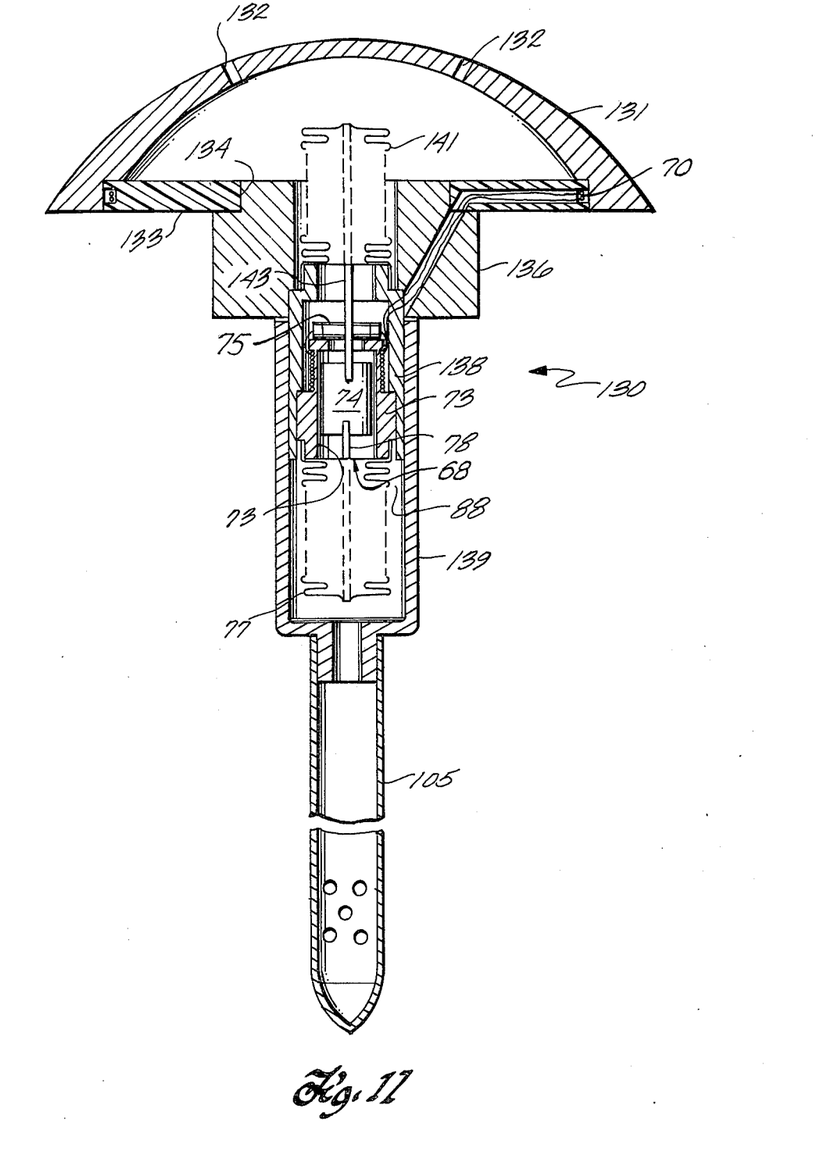
FIG. 11 is a sectional elevation of a double-coupled-bellows version of the transducer.

In applications demanding pressure measurement of maximum accuracy, it is desirable to modify the transducer subassembly described above by adding a means to reduce or eliminate spurious pressure indications resulting from changes in ambient barometric pressure (which directly influences the absolute pressure of body fluids) and also changes in body temperature. A preferred solution to this error-compensation problem is shown in FIG. 11 as an implantable pressure-sensing assembly 130.

Assembly 130 includes a dome-shaped cover 131 generally similar to cover 85 with the exception that a plurality of holes 132 are formed through the top or outer wall of the cover. A base 133 with a central opening 134 is secured and sealed to cover 131, and is generally similar to base 84 described above. A hollow tubular mounting boss 136 is fitted in opening 134, and is secured and sealed to base 133.

A hollow and open-ended tubular mounting shell 138 is secured and sealed within and extends from the distal end of boss 136, and sleeve 73 of a transducer subassembly 68 as already described is secured and sealed within shell 138. As in the configuration described above, an antenna coil 70 is wrapped around the periphery of base 133, and an intraventricular cannula 105 is secured to the distal end of a tubular extension 139 fitted over and secured to mounting shell 138.

The end of mounting shell 138 adjacent capacitor 75 at the end of the transducer subassembly remote from bellows 77 is necked down to receive and support in sealed relation a reference-volume compensating bellows 141 which has stiffness, area, and volume identical to bellows 77. The two bellows are in fluid communication, and they form opposite sealed ends of the internal or reference volume of the transducer subassembly. Bellows 77 is the primary pressure-sensing surface as it is immersed in fluid conducted through cannula 105, and bellows 141 is a compensating volume immersed in body fluid (forming between the scalp and skull when the assembly is surgically installed as described above) which floods the interior of cover 131 through holes 132.

The fluids surrounding bellows 77 and 141 are equally influenced by barometric-pressure variations and changes in body temperature. Partial error compensation is provided by the mere addition of the reference-volume bellows because an increase, for example, in barometric pressure will produce a greater increase in internal or reference pressure within the transducer due to a greater decrease in internal volume. This increase in reference pressure serves to limit the movement of bellows 77 and core 74, and the barometric error signal from the transducer is accordingly reduced.

The barometric and temperature errors are substantially eliminated by coupling the ends of the two bellows together by a rigid shaft 143 mounted similarly to shaft 78 but extending between core 74 and the closed end of bellows 141. In this configuration, the two bellows which have identical characteristics are identically and oppositely influenced by barometric or temperature variations, and no movement of core 74 occurs, thereby preventing the generation of an error signal.

The rigid connection of the bellows ends through core 74 and shafts 78 and 143 thus prevents any core movement in response to fluid-pressure variations (arising from changes in ambient barometric pressure or body temperaure) which affect both bellows equally. Some sacrifice in transducer sensitivity results from this substantially perfect error compensation, however, because the system stiffness of the transducer subassembly is increased by the addition of the coupled second bellows.

Figure 12:
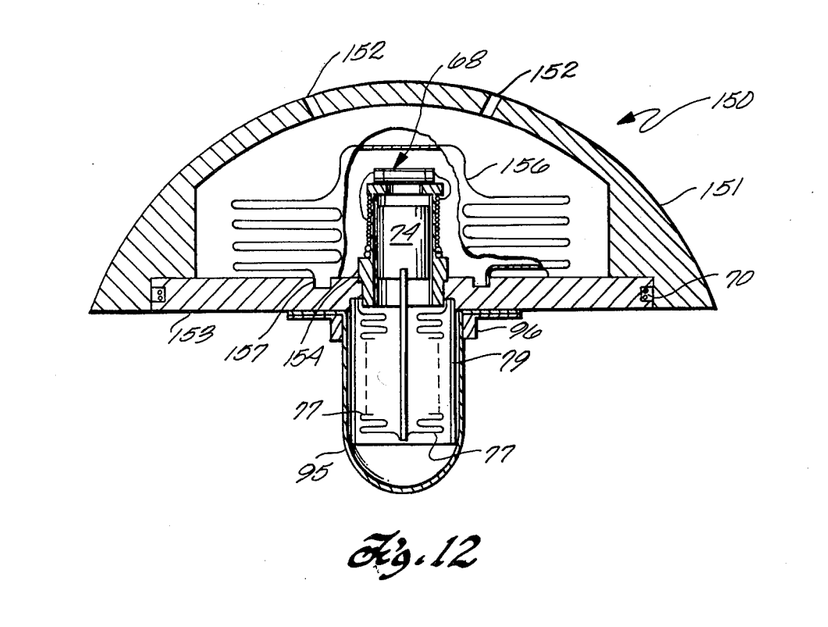
FIG. 12 is a sectional elevation of another style of double-bellows transducer.

If maximum sensitivity is required, a substantial reduction in barometric-pressure and body-temperature error signals is provided by an uncoupled dual-bellows assembly 150 as shown in FIG. 12 in a form suitable for measuring epidural pressure. This assembly includes a housing formed by a dome-shaped cover 151 with openings 152 therethrough, and a base 153 generally similar to base 84 and having a central opening 154. A transducer subassembly 68 is secured and sealed to base 153, and extends through opening 154. As described above, antenna coil 70 is wrapped around the periphery of the base.

A reference-volume or compensating bellows 156 is disposed within the housing over the end of the transducer subassembly, and is secured and sealed to an annular recess 157 in the inner face of base 153. Bellows 156 is thus in fluid communication with bellows 77 through the hollow interior of the transducer subassembly, but the two bellows are not mechanically coupled as in assembly 130 described above.

Bellows 156 is substantially larger in diameter than bellows 77, and is accordingly more sensitive to pressure variations because the increased diameter results in increased force-summing area and decreased mechanical stiffness. The objective of this arrangement is to make the internal reference pressure of the transducer "track" the external pressure acting on bellows 156 as closely as possible, and essentially perfect error compensation would be achieved with a completely "limp" compensating bellows. In practice, adequate compensation is achieved with bellows diameters which differ by a factor of about four or five.

Compensating bellows 156 is also useful in a configuration as shown in FIG. 9 where the transducer subassembly is remotely positioned with respect to the dome-shaped housing (which would be apertured to admit body fluid into the housing). Similarly, the relatively small-diameter coupled-bellows version shown in FIG. 11 can be shifted to the distal end of the transducer assembly to be positioned directly within a ventricle or other body cavity. These various elements form parts of a flexible building-block pressure-measuring system which can be arranged in specific configurations best suited to the geometry of the space in which measurements are to be made.

There has been described a compact variable-resonancefrequency pressure transducer using a variable capacitor or inductor controlled by pressure-sensing means such as a bellows. A significant improvement in transducer coupling to an external read-out system is provided by use of an inductively coupled antenna coil, and error signals from variations in environmental pressure and temperature are reduced or cancelled by addition of a variable-volume compensator to the reference volume of the transducer.

What is claimed is:

1. In a transducer adapted for implantation beneath the skin and having a resonant L-C circuit with capacitor and inductor elements, one of the elements being variable and driven by a mechanical force sensor whereby the circuit has a variable resonant frequency which is related to the magnitude of force sensed by the sensor, and the frequency can be determined without wired connection by a remote circuit, the transducer including a housing for supporting the circuit elements and force sensor, the housing having an end adapted to be positioned closer to the skin than the inductor element when the transducer is implanted; the improvement comprising a coupling coil positioned adjacent and inductively coupled to the inductor element, and an antenna coil connected across and spaced from the coupling coil, the antenna coil being positioned adjacent said housing end to be closer to the skin than the inductor element to enable enhanced transmission of electromagnetic energy between the remote circuit and the resonant L-C circuit through the antenna coil.

2. The improvement defined in claim 1 wherein the coupling coil has a substantially constant inductance which is unaffected by movement of the mechanical force sensor.

3. The improvement defined in claim 1 wherein the coupling and antenna coils have unequal diameters, the antenna coil having the larger diameter.

4. A wireless pressure transducer for implantation beneath the skin, comprising:
an implantable housing;
a resonant circuit mounted in the housing, and including capacitor and inductor elements, one of the elements being variable whereby the circuit has a variable resonant frequency, the housing having an end adapted to be positioned closer to the skin than the inductor element when the housing is implanted;
pressure-sensing means secured to the housing and mechanically connected to said variable element to vary the resonant frequency of the L-C circuit responsive to pressure changes;
a coupling coil positioned adjacent and inductively coupled to said inductor element; and
an antenna coil electrically connected across and spaced from said coupling coil to be positioned adjacent said housing end and close to the skin for enhanced inductive coupling of the resonant circuit to an external transmitting coil of a variable-frequency oscillator.

5. The transducer defined in claim 4 wherein the coupling and antenna coils have unequal diameters, the antenna coil having the larger diameter.

6. The transducer defined in claim 4 wherein the inductor element includes a tubular mandrel and a coil wound on the mandrel, and the coupling coil is wound on the mandrel immediately adjacent one end of the inductor-element coil.

7. The transducer defined in claim 6 wherein the inductor element is the variable element and includes a core movably positioned within said mandrel and connected to the pressure-sensing means to be within a portion of the inductor-element coil, and the coupling coil is positioned on the mandrel to be disposed around the core for all core positions in an operating range of the transducer.

8. The transducer defined in claim 7 wherein the housing includes a substantially circular base having a diameter substantially larger than the coupling coil, and the antenna coil is wound around the periphery of the base.

9. The transducer defined in claim 8 wherein the coupling and antenna coils have the same number of turns.

10. The transducer defined in claim 5 wherein the coupling coil has a substantially constant inductance which is unaffected by movement of the pressure-sensing means.

11. The transducer defined in claim 4 wherein the housing has a sealed interior volume defining a reference pressure for the transducer, said volume being variable with displacement of the pressure-sensing means resulting from application of an external pressure being measured, and further comprising a second variable-volume pressure-sensing means positioned within the housing and in fluid connection with the sealed interior volume, the several pressure-sensing means being exposed to different pressure media which are equally affected by variations in barometric pressure, and each pressure-sensing means being a bellows with a closed end positioned for exposure to the respective pressure medium being sensed.

12. The transducer defined in claim 11 wherein the two bellows are substantially identical, and further comprising a mechanical connecting means secured to and rigidly coupling together the two bellows ends.

13. The transducer defined in claim 11 wherein the two bellows are of unequal diameter and stiffness, the bellows forming said second means having a larger diameter and lower stiffness than the bellows forming said pressure-sensing means connected to said variable element.

* * * * *

UNITED STATES PATENT AND TRADEMARK OFFICE
CERTIFICATE OF CORRECTION

PATENT NO. : 4,127,110
DATED : November 28, 1978
INVENTOR(S) : Leo A. Bullara

It is certified that error appears in the above–identified patent and that said Letters Patent are hereby corrected as shown below:

Column 11, line 15  1 should read 3.

Signed and Sealed this

First Day of April 1980

[SEAL]

Attest:

SIDNEY A. DIAMOND

Attesting Officer

Commissioner of Patents and Trademarks